United States Patent [19]

Pietsch et al.

[11] Patent Number: 4,831,065

[45] Date of Patent: May 16, 1989

[54] ANTITHROMBOGENIC, NON-CALCIFYING MATERIAL AND METHOD OF MAKING ARTICLES FOR MEDICAL PURPOSES

[75] Inventors: Hanns Pietsch; Holger Kartheus, both of Hamburg; Hans-Joachim Holtzmann, Hamburg; Günther Sachau, Quickborn; Helmut Reul, Düren, all of Fed. Rep. of Germany

[73] Assignee: Beiersdorf Aktiengesellschaft, Hamburg, Fed. Rep. of Germany

[21] Appl. No.: 933,003

[22] Filed: Nov. 20, 1986

[30] Foreign Application Priority Data

Nov. 23, 1985 [DE] Fed. Rep. of Germany .... 3541478.2

[51] Int. Cl.⁴ .................. C08L 75/08; C08K 5/11
[52] U.S. Cl. ..................... 523/112; 525/440; 525/454; 525/460; 524/308; 524/312; 524/315; 524/317; 524/318; 524/590
[58] Field of Search ............... 523/112; 524/308, 312, 524/315, 317, 318, 590; 525/452, 454, 440

[56] References Cited

U.S. PATENT DOCUMENTS

| | | | |
|---|---|---|---|
| 3,309,261 | 3/1967 | Schiller et al. | 525/454 |
| 4,093,673 | 6/1978 | Chang et al. | 525/454 |
| 4,160,851 | 7/1979 | Lienet et al. | 427/302 |
| 4,350,806 | 9/1982 | Wagener | 528/289 |
| 4,371,686 | 2/1983 | Yamamoto et al. | 528/76 |
| 4,429,082 | 1/1984 | Lee et al. | 525/454 |
| 4,521,564 | 6/1985 | Solomon et al. | 525/452 |
| 4,528,343 | 7/1985 | Kira | 528/28 |
| 4,555,443 | 11/1985 | Kitugawa et al. | 428/408 |
| 4,582,873 | 4/1986 | Gao et al. | 524/591 |
| 4,597,362 | 6/1986 | Smith et al. | 521/52 |
| 4,600,652 | 7/1986 | Solomon et al. | 428/423.3 |

FOREIGN PATENT DOCUMENTS

| | | | |
|---|---|---|---|
| 38813 | 3/1982 | Japan | 525/457 |
| 35812 | 9/1984 | Japan | 524/315 |
| 2072206 | 9/1981 | United Kingdom | 523/112 |

OTHER PUBLICATIONS

WO84/01879-U.S.-Dated May 24, 1984-Surfactant Treatment of Implantable Biological Tissue to Inhibit Calcification-PCT/US83/01703.

Primary Examiner—Lewis T. Jacobs
Assistant Examiner—David W. Woodward
Attorney, Agent, or Firm—Sprung Horn Kramer & Woods

[57] ABSTRACT

An antithrombogenic, non-calcifying, and elastic material on a basis of polyurethane, characterized by the addition of fatty-acid esters and optionally by the further addition of cross-linking agent that react with water.

7 Claims, No Drawings

ANTITHROMBOGENIC, NON-CALCIFYING MATERIAL AND METHOD OF MAKING ARTICLES FOR MEDICAL PURPOSES

BACKGROUND OF THE INVENTION

The present invention relates to an antithrombogenic, non-calcifying, and elastic material on a basis of polyurethane and to a method of manufacturing articles for medical purposes that are appropriate for remaining in contact with human blood in both short-term and long-term use.

That polyurethanes are appropriate—due to such mechanical properties as elasticity, flexibility, tear-resistance, and to a certain extent antithrombogenicity—for the manufacture of such articles as prosthetic cardiac valves, coatings on cardiac-pacemaker electrodes, blood-storage bags, catheters, etc. is known. A long series of patents and patent applications (e.g. German patent No. 1 944 969, German OS No. 2 642 616, German OS No. 3 107 542, German OS No. 3 130 646, German OS No. 3 318 730, German OS No. 3 606 440, European patent No. 68 385, EPA No. 152 699, EPA No. 184 465, U.S. Pat. No. 4,350,806, U.S. Pat. No. 4,371,686, and U.S. Pat. No. 4,600,652) concerned with improving or optimizing the blood-compatibility in particular of the polyurethanes by means of additives or specially selected components have been published.

It has in the meantime, however, been shown that the blood compatibility of the materials, primarily their antithrombogenic action, is not the only critical point, but that calcification deposits and, in long-term application, biological breakdown are at least equivalent problems.

Washing what are called bioprostheses, which consist of natural tissue preferably cross-linked with glutaraldehyde, in an aqueous solution of alkyl sulfates (Eur. Pat. No. 65 827) or of water-soluble salts of alkylphosphorates like sodium dodecylhydrogen phosphate (U.S. Pat. No. 4,402,697) to prevent calcification is known. These methods, however, cannot be transferred to implants like polyurethane prosthetic cardiac valves because the salts do not attach to polyurethanes.

SUMMARY OF THE INVENTION

One object of the present invention is accordingly to improve polyurethanes, which are in themselves known, whether polyether urethanes, polyester urethanes, polyetherurethane ureas, or polyester-urethane ureas or their known mixtures or mixed polymers thereof and of modifying compounds, to the extent that they will also have a non-calcifying action, meaning that, even during long-term residence in the body, no or almost no calcification will deposit on products manufactured therefrom.

It has, surprisingly, been found that this object can be attained by the addition of fatty-acid esters, preferably fatty-acid esters of aliphatic, unbranched, saturated, or singly or doubly unsaturated monocarboxylic acids with 10 to 20 carbon atoms and monovalent or polyvalent aliphatic alcohols with 1 to 6 carbon atoms or even polyoxyethylene fatty-acid esters and polyoxyethylene-sorbitane fatty-acid esters, to the polyurethanes.

These fatty acids are primarily acids like lauric acid, oleic acid, palmitic acid, and myristic acid, and the alcohols compounds like methyl alcohol, ethanol, propyl alcohol, isopropyl alcohol, 1-butanol, 2-butanol, 1-isobutyl alcohol, 2-isobutyl alcohol, 2-methyl-2-propanol, ethanediol, 1,2-propanediol, 1,3-propanediol, ascorbic acid, glycerol, and sorbitane. The last two can also be doubly or triply esterified.

Especially appropriate polyoxyethylene fatty-acid esters and polyoxyethylene-sorbitane fatty-acid esters are polyoxyethylene monostearate and polyoxyethylene-sorbitane monooleate.

The esters must have at least one fatty-acid group and are preferably selected for their compatibility with the particular polyurethane, meaning that they will not cloud it when added in liquid form. The esters should also exhibit satisfactory tissue compatibility, which improves as water solubility decreases.

Also among the preferred esters are compounds that are already permitted and conventional as drug adjuvants, like isopropyl myristate and palmitate, ascorbyl palmitate, and sorbitane monolaurate, monooleate, monopalmitate, and monostearate.

From 0.1 to 10% and preferably from 0.5 to 5% by weight of the esters are added to the mixture in terms of the overall weight to obtain a satisfactory anticalcification action.

The polyurethanes in question are primarily linear and thermoplastic compounds, optionally soluble in organic solvents, whereby the chemical composition of the polyurethane determines the type of solvent. Examples of often appropriate solvents are N,N-dimethyl formamide and N,N-dimethyl acetamide and mixtures thereof or with other organic solvents.

Preferably employed are linear, segmented polyether-urethane ureas and polyester-urethane urea. These contain urea groups in addition to the urethane groups.

They are prepared in a way that is in itself known by converting polyethers or polyesters with terminal hydroxyl groups into prepolymers with terminal isocyanate groups using diisocyanate compounds and then converting these into high-molecular polyether-urethane or polyester-urethane ureas using appropriate diamino compounds.

Preferable for the polyethers that constitute the soft segment are polyethylene glycol, 1,2-polypropylene glycol, 1,3-polypropylene glcyol, the copolymer of polyethylene glycol and 1,2-polypropylene glycol, and (1,4)-polybutylene glycol or their mixtures, whereby the polyethers should have a mean molecular weight of 500 to 20,000 and preferably of 800 to 5000.

Preferable for the polyesters that constitute the soft segment are compounds of aliphatic dicarboxylic acids with aliphatic diols with 2 to 10 methylene groups like for example compounds of malonic, succinic, glutaric, adipic, pimilic, suberic, azelaic, sebacic, or even terephthalic acid with the alcohols glycol, diglycol, 1,2-dihydroxypropane, 1,3-dihydroxypropane, 1,4-dihydroxybutane, 1,5-dihydroxypentane, 1,6-dihydroxyhexane, 1,7-dihydroxyheptane, 1,8-dihydroxyoctane, 1,9-dihydroxynonane, or 1,10-dihydroxydecane.

The polyesters should preferably have a mean molecular weight of 500 to 20,000 and preferably 800 to 10 000.

Preferred diisocyanate and diamino constituents are compounds that derive from diphenylmethane, containing, that is, between the phenyl nuclei an active methylene group like 4,4'-diisocyanatophenylmethane or 4,4'-diaminodiphenylmethane for example. Other diisocyanates, however, like 1,6-hexamethylene diisocyanate, 2,4-toluylene diisocyanate, 2,6-toluylene diisocyanate, 1,4-phenylene diisocyanate, 1,2-phenylene diisocyanate, 4,4'-dicyclohexylmethane diisocyanate, isophorone diisocyanate, methylcyclohexyl diisocyanate, p-xylylene diisocyanate 1-chloro-2,4-phenylene diisocyanate, trimethylhexamethylene diisocyanate, 4,4'-diisocyanato-3,3'-dimethyldiphenylmethane, and 4,4'-diisocyanato-3,3'-dimethylbiphenyl, can also be employed.

Other appropriate diamino compounds that should be mentioned by way of example are diaminobenzene, diaminotoluene, and p,p'-isopropylidene di(phenylamine).

Another drawback to the polyurethanes employed up to now is their biological breakdown due to hydrolysis and enzymatic action, especially when the products made out of them are used over the long term. The ester bonds in polyester urethane can be split by esterases, the urethane bonds by proteases, and the urea bonds by ureases. Breakdown phenomena of this type, which have been studied in various bloodcompatible polyurethanes, occur at a rate that varies somewhat as a function of the hydrophilia of the particular polyurethane, commence at the surface, and lead to erosion and furrowing of the originally smooth surface. This surface roughness then constitutes a mechanical site of attack for deposits of blood and lime. The breakdown also lowers the mechanical stability of the product.

Another object of the invention accordingly is to counteract this tendency to break down.

This object is attained by using cross-linked polyurethane, proceeding in a practical way in accordance with the invention by shaping the material before it is cross-linked, either thermoplastically, by injection molding for example, or from solution and then cross-linking the shaped product through the action of water or humidity. The cross-linkage makes the urethane insoluble in the solvents that it was previously soluble in.

The cross-linkage is preferably conducted with alkoxysilyl compounds that contain at least two methoxysilyl, ethoxysilyl, propoxysilyl, or butoxysilyl groups and at least one amino group, preferably with Y-aminopropyl tris-ethoxysilane. Other cross-linking agents for example are N-aminoethyl -aminopropyl trimethoxysilane and what is called "triaminosilane" ($H_2N-CH_2-CH_2-NH-CH_2-CH_2-NH-CH_2-CH_2-CH_2-Si(OR)_3$, wherein $R = -CH_3$ or $-C_2H_5$).

From 0.1 to about 5% by weight of the cross-linking agents, depending on the polyurethane and the desired properties of the final product, should be added in terms of the weight of the polyurethane in order to attain adequate resistance to breakdown.

Preferred mixtures contain 85 to 99.9% by weight of the polyurethanes, 0.1 to 10% by weight of the aforesaid fatty-acid ester, and optionally up to 5% by weight of the cross-linking agent, all in terms of the total weight of the mixture.

A method of manufacturing articles for medical purposes from the new materials has also been developed in accordance with the invention, with special attention devoted to purifying the materials to remove toxic monomers, oligomers, and adjuvants.

This method essentially comprises the steps that will now be described.

Once the polyurethanes have been prepared by known methods (as described for example in U.S. Pat. No. 2,929,804) either from or without a solution, the residual monomers, oligomers, and catalysts are extracted. The extraction agents are organic solvents that will dissolve the latter but not the polymers. Solvents of this type include for instance methyl alcohol, ethanol, isopropyl alcohol, acetone, butanone, hexane, n-octane, isooctane, cyclohexane, benzene, toluene, methyl, ethyl, and isopropyl formate, methyl, ethyl, and isopropyl acetate, methyl, ethyl, and isopropyl propionate, and preferably ethyl acetate.

The washing proceeds in accordance with the invention by extraction at room temperature below 30° C. Any adhering solvent is then removed by drying at below 30° C. If the processing is to be carried out by immersion lacquering (immersion coating), the purified polyurethane is dissolved in an appropriate solvent. The dissolution should be carried out with as little temperauure stress as possible, preferably at below 30° C., which is, however, not always possible. The fatty-acid ester and optionally the cross-linking agent, both of them in liquid form, can then be worked into this solution.

If the material is to be treated thermoplastically, the fatty-acid esters and optionally the cross-linking agent can be mixed with the solid polyurethane. Depending on the form of the polyurethane—powder, pellet, granulate, or fiber—the fatty-acid esters and optionally the cross-linking agents can be added to the urethane in a mixing drum or through an appropriate controlled-flow device.

Since the cross-linking agents in accordance with the invention are sensitive to water and humidity, the mixture must be stored before processing protected from premature cross-linking due to moisture.

Further processing can be carried out either from solution or without solvent by exploiting the thermoplastic properties of the material. When a solvent is employed, the shape of the future product, the atrioventricular valves of a prosthetic cardiac valve for example, can be immersed once or preferably several times in the solution of polyurethane and additives and thoroughly dried each time at temeeratures between 30° and 60° C. and a relative humidity of 20%, with the mold kept constantly rotated to ensure a uniform coating thickness. This is followed by thorough drying and treatment with deionized and, if necessary, sterilized water. This treatment extracts the remaining water-extractable substances from the article and allows cross-linkage when a cross-linking agent is present.

If the processing is thermoplastic, in an injection molder, extruder or calender, or deep-drawing machine, for example, the articles ae treated with water in the same way once they have attained their final shape.

The mixtures and methods in accordance with the invention will lead to outstandingly blood-compatible and non-calcifying articles. The cross-linked variant is also especially appropriate for long-term use, in flexible prosthetic cardiac valves, in blood pumps ("artificial hearts"), as membranes, as coatings for cardiac-pacemaker electrodes, for angiographic or cardiac catheters, as artificial pericardia, and as materials for tubing and valves or bags that come into contact with the blood.

The satisfactory mechanical properties of the polyurethanes are unchanged by the additives in accordance with the invention. It is accordingly their biochemical and not their mechanical properties that are mentioned in the examples.

The overall cellular and tissue compatibility of the materials was tested with 3T3 cell cultures. Hemolysis was determined in accordance with ASTM Standard F 756. Blood compatibility was tested in vitro as described by J. P. Fischer, P. Fuhge, K. Burg, and N. Heimburger in "Methoden zur Herstellung und Charakterisierung von Kunststoffen mit verbesserter Blutvertraglichkeit," *Angew. Makromol. Chem.* 105 (1982), 331-65.

The anticalcification properties were tested as described by B. Glasmacher, H. Reul, G. Rau, C. Erckes, and J. Wieland in "In-vitro investigation of the calcification behaviour of polyurethane biomaterials," lecture, International Polyurethanes in Biomedical Engineering Congress, June 18 & 18, 1986.

DESCRIPTION OF THE PREFERRED EMBODIMENTS

The invention will now be specified through the following examples.

EXAMPLE 1

Starting polyurethane 1100 g of fibers of thermoplastic polyurethane urea (Du Pont Lycra T137C) were treated with 7 l of ethyl acetate, extracted 24 hours at 15° to 25° C., and dried at room temperature. The weight loss was approximately 8 to 11%. The extracted and dried fibers were dissolved at room temperature in dimethyl acetamide to form a 10% solution—the starting polyurethane 1 (SPU 1) employed in the subsequent examples.

EXAMPLES 2 TO 5

The starting-polyurethane solution prepared as described in Example 1 was treated with various fatty-acid esters as described in the following table.

| Ex. | SPU 1 (%, wt) | Fatty-acid ester (%, wt) |
|---|---|---|
| 2 | 97.0 | 3.0 isopropyl palmitate |
| 3 | 95.0 | 5.0 butyl laurate |
| 4 | 99.5 | 0.5 sorbitane trioleate |
| 5 | 97.0 | 3.0 polyoxyethylene monostearate |

Sheeting 0.3 mm thick was poured from these solutions containing the fatty-acid esters in a cleanroom subject to dust-free conditions. The sheets were transparent and smooth-surfaced. Their blood compatibility was tested by the method described by Fischer et al. and was better in every case than that of the starting polyurethane prepared as described with reference to Example 1.

Calcification was tested by the method described by Glasmacher et al. and was better in every case than that of the starting polyuurethane prepared as described with reference to Example 1.

EXAMPLES 6 TO 8

The starting-polyurethane solution prepared as described in Example 1 was treated with various fatty-acid esters and cross-linking agents as described in the following table.

| Ex. | SPU 1 (%, wt) | Fatty-acid ester (%, wt) | Cross-linking agent (%, wt) |
|---|---|---|---|
| 6 | 96.0 | 3 isopropyl palmitate | 1.0 γ-aminopropyl tris-ethoxysilane |
| 7 | 96.5 | 3 polyoxy-ethylene-sorbitane monooleate | 0.5 n-aminoethyl-aminopropyl trimethoxysilane |
| 8 | 93.0 | 5 ethyl laurate | 2.0 "triaminosilane" ($H_2N-CH_2-CH_2-NH-CH_2-CH_2-NH-CH_2-CH_2-CH_2-Si(OCH_3)_3$) |

Sheeting was also poured from these solutions in a cleanroom subject to dust-free conditions. Once the solvent had been evaporated from the sheets, they were left in deionized water at 60° C. for 24 hours and dried. They were then tested for cross-linkage by treating them with dimethyl acetamide and vibrating them in a shaker for 24 hours. All of these sheets were insoluble, whereas those poured as described with reference to Examples 2 through 5 were soluble when subjected to the same test.

When the sheets were tested for blood compatibility and calcification, the results were also better than those for a sheet poured from the starting polyurethane poured as described with reference to Example 1.

EXAMPLE 9

1100 of granulated polyether urethane (Pellethane 2363-80A) were treated with 7 l ethyl acetate and extracted and dried 24 hours at 15° to 25° C. The weight loss was 1 to 2%. The extracted and dried polyurethane was dissolved in a mixture of dimethyl formamide and xylene (o/p-mixture in a ratio of 1:1 by weight) 30 hours at 100° C. The solution contained less than 1% insoluble constituents, which were filtered out.

This clear and slightly yellowish solution was employed as the starting polyurethane 2 (SPU 2) in the following examples.

EXAMPLES 10 TO 16

The starting polyurethane 2 prepared as described with reference to Example 9 was treated with various fatty-acid esters as described in the following table.

| Ex. | SPU 2 (%, wt) | Fatty-acid ester (%, wt) |
|---|---|---|
| 10 | 96.0 | 4.0 ethyl laurate |
| 11 | 90.0 | 10.0 sorbitane monooleate |
| 12 | 92.0 | 8.0 ascorbyl palmitate |
| 13 | 99.0 | 1.0 isopropyl myristate |
| 14 | 97.0 | 3.0 isopropyl palmitate |
| 15 | 95.0 | 5.0 butyl laurate |
| 16 | 99.5 | 0.5 polyoxyethylene-sorbitane monooleate |

Sheeting was poured from these solutions in a cleanroom subject to dust-free conditions. Tests for blood compatibility and calcification again produced results that were better than those for a sheet poured from the starting polyurethane 2 poured without additives as described with reference to Example 9.

EXAMPLE 17

1100 g of granulated polyester urethane (Estane 58 206) was treated with 7 l of ethyl acetate and extracted and dried 24 hours. The extracted and dried polyurethane was extruded into a billet 2 mm thick and 2 cm wide. Samples for testing blood compatibility and calcification were cut from this starting polyurethane 3 (SPU 3).

EXAMPLES 18 TO 21

Mixtures of the purified starting polyurethane 3 from Example 17 with various fatty-acid esters were prepared in an extruder.

| Ex. | SPU 3 (%, wt) | Fatty-acid ester (%, wt) |
|---|---|---|
| 18 | 97 | 3 isopropyl palmitate |
| 19 | 97 | 3 butyl laurate |
| 20 | 97 | 3 isopropyl myristate |
| 21 | 97 | 3 ascorbyl palmitate |

The mixtures were extruded into billets, and samples for testing blood compatibility and calcification were cut therefrom. In this case as well the properties of the materials prepared in accordance with Examples 18 through 21 were superior to those of the untreated material.

The present specification and claims are of course intended solely as illustrative of one or more potential embodiments of the invention and should not be construed as limiting it in any way. The invention may accordingly be adapted and modified in many ways without deviating from the theory behind it or exceeding its scope of application.

What is claimed is:

1. A composition suitable for producing a medical device which in use comes into contact with blood consisting essentially of a polyurethane, a fatty acid ester and an alkoxysilyl crosslinking agent which contains at least two methoxysilyl, ethoxysilyl, propoxysilyl, or butoxysilyl groups and at least one amino group, the cross-linking agent being present in about 0.1 to 5% by weight of the polyurethane, the device produced therefrom being antithrombogenic, non-calcifying and elastic.

2. A composition according to claim 1, wherein the fatty acid ester is an ester of an aliphatic, unbranched, saturated, or singly or doubly unsaturated monocarboxylic acid with 10 to 20 carbon atoms and a monovalent or polyvalent aliphatic alcohol with 1 to 6 carbon atoms or ascorbic acid, a polyoxyethylene fatty-acid ester, or a polyoxyethylene-sorbitane fatty acid ester.

3. A composition according to claim 1, wherein the ester is present in about 0.1 to 10% by weight of the polyurethane.

4. A composition according to claim 1, wherein the ester is present in about 0.5 to 5% by weight of the polyurethane.

5. A composition according to calim 1, wherein the polyurethane is crosslinked.

6. A composition according to claim 1, wherein the fatty acid ester is an ester of an acid selected from the group consisting of lauric acid, oleic acid, palmitic acid, myristic acid and stearic acid, and an alcohol selected from the group consisting of methyl alcohol, ethanol, propyl alcohol and polyoxyethlene-sorbitane.

7. A composition according to claim 1, wherein the fatty acid ester is selected from the group consisting of isopropyl palmitate, butyl laurate, sorbitane trioleate, polyoxyethylene monostearate, polyoxyethylene-sorbitane monooleate, ethyl laurate, sorbitane monooleate, ascorbyl palmitate and isopropyl myristate.

* * * * *

UNITED STATES PATENT AND TRADEMARK OFFICE
CERTIFICATE OF CORRECTION

PATENT NO. : 4,831,065
DATED : May 16, 1989
INVENTOR(S) : Pietsch et al

It is certified that error appears in the above-identified patent and that said Letters Patent is hereby corrected as shown below:

Title page: U.S. PATENT DOCUMENTS Add --4507418  8/1985  Utsunomiya et al
"4582873" delete "Gao" and substitute
--Gaa--

Signed and Sealed this

Fifth Day of June, 1990

Attest:

HARRY F. MANBECK, JR.

Attesting Officer      Commissioner of Patents and Trademarks